United States Patent [19]

Wolpe et al.

[11] Patent Number: 5,650,147
[45] Date of Patent: Jul. 22, 1997

[54] METHODS OF STIMULATING GRANULOCYTE-MACROPHAGE PROGENITOR CELLS

[75] Inventors: Stephen D. Wolpe, Arlington, Mass.; Anthony Cerami, Shelter Island; Barbara Sherry, New York, both of N.Y.

[73] Assignee: The Rockefeller University, New York, N.Y.

[21] Appl. No.: 207,887

[22] Filed: Mar. 7, 1994

Related U.S. Application Data

[63] Continuation of Ser. No. 377,937, Jul. 10, 1989, abandoned, which is a continuation-in-part of Ser. No. 240,078, Sep. 2, 1988, abandoned, and a continuation-in-part of Ser. No. 238,937, Sep. 2, 1988, abandoned, each is a continuation-in-part of Ser. No.104,827, Oct. 2, 1987, abandoned, which is a continuation-in-part of Ser. No. 766,852, Aug. 16, 1985, abandoned, which is a continuation-in-part of Ser. No. 414,098, Sep. 7, 1982, Pat. No. 4,603,106, which is a continuation-in-part of Ser. No. 351,290, Feb. 22, 1982, abandoned, which is a continuation-in-part of Ser. No. 299,932, Sep. 8, 1981, abandoned.

[51] Int. Cl.$^6$ .................................................. A61K 38/19
[52] U.S. Cl. ............................................................ 424/85.1
[58] Field of Search ........................ 514/2, 12; 424/85.1; 530/350, 351; 435/69.5, 69.6

[56] References Cited

U.S. PATENT DOCUMENTS

| | | | |
|---|---|---|---|
| 4,504,586 | 3/1985 | Nicolson | 436/518 |
| 4,603,106 | 7/1986 | Cerami et al. | 435/72 |
| 4,961,926 | 10/1990 | Gabrilove | 424/85.1 |
| 5,145,676 | 9/1992 | Fahey, III et al. | 424/85.1 |
| 5,306,709 | 4/1994 | Gewirtz | 514/12 |

FOREIGN PATENT DOCUMENTS

WO 83/00930  3/1983  WIPO.

OTHER PUBLICATIONS

Mizel, et al., 1981 "Purification to apparent homogeneity of murine interleukin 1." J. Immunol. 126:834–7.
Wolpe, et al., 1988, "Macrophages secrete a novel heparin--binding . . . " J. Exp. Med. 167:570–581.
Davatelis, et al., 1988, "Cloning and Characterization of a cDNA . . . " J. Exp. Med. 167: 1939–1944.
Sherry et al. (1992) Cytokines 4: 117–30.
Sherry et al. (1991) Curr. Opin. Immunol. 3: 56–60.
Widmer et al. (1991) J. Immunol. 146:4031–40.
Baker et al. (1990) Nucl. Acids Res. 18: 6453.
Dexter et al. (1990) Nature 344: 380–1.
Graham et al. (1990) Nature 344:442–4.
Haskill et al. (1990) Proc. Natl. Acad. Sci. USA 87:7732–6.
Brown et al. (1989) J. Immunol. 142: 679–87.
Davatelis et al. (1989) Science 243: 1066–8.
Wolpe et al. (1989) FASEB J. 3: 2565–73.
Wolpe et al. (1989) Proc. Natl. Acad. Sci. USA 86:612–16.
Yoshimura et al. (1989) FEBS Letts. 224:487–93.
Zipfel et al. (1989) J. Immunol. 142: 1582–90.
Lipes et al. (1988) Proc. Natl. Acad. Sci. USA 85: 9704–8.
Matsushima et al. (1988) J. Exp. Med. 167: 1883–93.
Ottman et al. (1988) J. Immunol. 14: 2661.
Richmond et al. (1988) EMBO J. 7: 2025–31.
Sherry et al. (1988) J. Exp. Med. 168: 2251–9.
Sing et al. (1988) Blood 72: 1504–11.
Vlassara et al. (1988) Science 240: 1546–8.
Anisowicz et al. (1987) Proc. Natl. Acad. Sci. USA: 7188–92.
Sassa et al. (1987) Blood Cells 13: 161–9.
Williams et al. (1987) Exp. Hematol. 15: 243–50.
Williams et al. (1987) Exp. Hematol 15: 1007–12.
Wolpe et al. (1987) in *The inhibitors of hamatopoiesis*. Najman et al. eds. pp. 197–200.
Yoshimura et al. (1987) J. Immunol. 139: 788–93.
Yoshimura et al. (1987) Proc. Natl. Acad. Sci. USA 84: 9233–7.
Caput et al. (1986) Proc. Natl. Acad. Sci. USA 83: 1670–4.
Reeves et al. (1986) Proc. Natl. Acad. Sci. USA 83: 3228–32.
Kownatzki et al. (1986) Clin. Exp. Immunol. 64: 214–22.
Obaru et al. (1986) J. Biochem. 99: 885–94.
Beutler et al. (1985) J. Exp. Med. 161: 984–95.
Beutler et al. (1985) Science 229: 869–71.
Mahoney et al. (1985) J. Immunol. 134: 1673–1675.
Beutler et al. (1985) Nature 316: 552–4.
Torti et al. (1985) Science 229:867–9.
(1984) Fundamental Immunology. W.E. Paul ed. p. 706.
Hotez et al. (1984) Parasite Immnuol. 6:203.
Lomdedico et al. (1984) Nature 312: 458–62.
Kawakami et al. (1982) Proc. Natl. Acad. sci. USA: 79: 912–16.
Deuel et al. (1981) Proc. Natl. Acad. Sci. 78: 4584–7.
Kawakami et al. (1981) J. Exp. Med. 154: 631–9.
Suggs et al. (1981) Proc. Natl. Acad. Sci. USA 78: 6613–17.
Merrill et al. (1980) J. Clin. Invest. 65: 268–76.
Kampschmidt et al. (1980) J. Lab. Clin. Med. 95:616–23.
Tono-Oka et al. (1980) Immnunol. 39: 607–13.

*Primary Examiner*—Marianne P. Allen
*Attorney, Agent, or Firm*—Klauber & Jackson

[57] ABSTRACT

The present invention relates to the identification of promoters of myelopoietic blood cell production. In particular, an agent has been discovered that enhances myelopoietic colony stimulating factor activity. The agent comprises cytokines that are also capable of binding to heparin, and inducing localized inflammation characterized by polymorphonuclear cell infiltration when administered subcutaneously. Particular agents comprise the inflammatory cytokines MIP-1 and MIP-2. Diagnostic and therapeutic utilities are proposed, and pharmaceutical compositions are likewise set forth.

8 Claims, 2 Drawing Sheets

METHODS OF STIMULATING GRANULOCYTE-MACROPHAGE PROGENITOR CELLS

RELATED APPLICATIONS

This application is a continuation of application Ser. No. 07/377,937, filed Jul. 10, 1989, now abandoned, which is a Continuation-In-Part of application Ser. Nos. 240,078 now abandoned and 238,937 now abandoned both filed Sep. 2, 1988 each of which is a Continuation-In-Part of application Ser. No. 104,827, filed Oct. 2, 1987 now abandoned, which is in turn a Continuation-In-Part of application Ser. No. 766,852, filed Aug. 16, 1985 now abandoned, which is in turn a Continuation-In-Part of Ser. No. 414,098, filed Sep. 7, 1982, now U.S. Pat. No. 4,603,106, issued Jul. 29, 1986, which is in turn a Continuation-In-Part of Ser. No. 351,290, filed Feb. 22, 1982, now abandoned, which is in turn a Continuation-In-Part of Ser. No. 299,932, filed Sep. 8, 1981, also abandoned. Applicants claim the benefit of these applications under 35 U.S.C. Section 120.

The research leading to the present invention was funded in part by grants from the National Institutes of Health and the Rockefeller Foundation.

BACKGROUND OF THE INVENTION

Myeloid blood cell production initiating from hematopoietic stem and progenitor cells is regulated by a network of interacting accessory cell populations. Broxmeyer, H. E. and Williams, D. E., "The Production of Myeloid Blood Cells and Their Regulation During Health and Disease," CRC CRIT. REV. ONCOL./HEMATOL. 8:173 (1985). Accessory cells release biomolecules or cytokines which in turn can act either directly on hematopoietic stem and progenitor cells or indirectly through action on other accessory cells. Certain cytokines have already been implicated in the modulation of blood cell production. These include, but are not limited to, the hematopoietic colony stimulating factors (CSF): granulocyte-macrophage (GM)-CSF, macrophage (M)-CSF or CSF-1, granulocyte (G)-CSF, multi-CSF (also termed interleukin (IL)-3) and erythropoietin, as well as IL-1 through IL-6, the tumor necrosis factors-alpha and beta, the interferons,-alpha, beta and gamma, transforming growth factor-beta, E-type prostaglandins 1 and 2, lactoferrin, acidic isoferritin, activin and inhibin. Individual cytokines can act on more than one cell type and can have more than one effect. New cytokines continue to be described, and new functions are being attributed to them, as well as to previously described cytokines.

SUMMARY OF THE INVENTION

In accordance with the present invention, certain materials have been determined to possess a promoting effect upon colony stimulating factor (CSF) activity. The materials determined to possess this activity comprise cytokines that possess the activity profiles of two species of inflammatory cytokines that were disclosed in co-pending application Ser. Nos. 238,937 now abandoned, and 240,078 now abandoned. These materials are newly discovered isolates of the mediator substance disclosed in U.S. Pat. No. 4,603,106, and comprise proteins that have been purified. The cytokines of the present invention exhibit the additional ability to bind to heparin, even at high salt concentrations, and to induce localized inflammation characterized by polymorphonuclear cell infiltration when administered subcutaneously.

In particular, two specific previously identified cytokines, MIP-1 and MIP-2 exhibit a promotihg effect on the colony and cluster formation activities of granuloctye-macrophage progenitor cells (CFU-GM) from the bone marrows of normal mice and humans that were also stimulated with sub-optimal concentrations of known colony stimulating factors.

In a first aspect of the invention, an agent for promoting myeloid blood cell production is defined which comprises a cytokine capable of enhancing myelopoietic colony and cluster formation, binding to heparin even at high salt concentrations, and inducing localized inflammation when administered subcutaneously. Pharmaceutical compositions are also contemplated which would comprise the agent of the present invention, or a suitable binding partner if appropriate, and a pharmaceutically acceptable carrier.

In a second aspect thereof, the present invention comprises a method for promoting myeloid blood cell production comprising administering an effective amount of an agent for enhancing myeloid blood cell colony and cluster formation, comprising the agent, or a pharmaceutical composition of the present invention.

Pharmaceutical compositions may be prepared in accordance with the invention and comprise a therapeutically effective amount of the present agent and a pharmaceutically acceptable diluent or carrier. The agent may preferably be present in amounts effective to deliver at least 100 ng/ml and preferably from about 100 ng/ml to about 200 ng/ml thereof.

In the instance where the production of myelopoietic blood cells may be beneficially monitored, such as to identify suspected blood disorders affecting cell production, the present invention contemplates a method for measuring the activity of the agent of the present invention. The method comprises retrieving a sample of bone marrow from a patient in which such disorder is suspected, and incubating the sample with a quantity of the agent of the present invention bearing an appropriate detectable label. The sample may thereafter be examined to determine whether such aberrant cellular activity is due to a deficiency in colony stimulating factor presence or activity, and to thereby attempt to isolate and identify the cause of such disorder. The present invention may accordingly extend to appropriate test kits including the agent of the present invention.

In a further embodiment, the present invention relates to certain therapeutic methods which would be based upon the activity of the agent, or upon other agents or drugs determined to possess the same activity. The therapeutic method based on the promotion of myeloid blood cell production in mammals, comprises administering either an agent or like material capable of enhancing myeloid colony stimulating factor activity, either individually or in mixture with each other in an amount effective to promote blood cell production in the host.

More specifically, the therapeutic method generally referred to herein could include the method for the treatment of myeloid blood cell production dysfunction by the administration of pharmaceutical compositions that may comprise effective quantities of the agent, or other equally effective drugs.

Accordingly, it is a principal object of the present invention to provide an agent that promotes myeloid blood cell production by enhancing myelopoietic colony stimulating factor activity.

It is a further object of the present invention to provide a method for measuring the activity of the agent as aforesaid, that also serves to evaluate possible disorders in blood cell production.

It is a further object of the present invention to provide pharmaceutical compositions for use in therapeutic methods which comprise or are based upon the agent or its binding partner(s).

It is a still further object of the present invention to provide a method for promoting myeloid blood cell production by the administration of the agent or a pharmaceutical composition as aforesaid.

It is a still further object of the present invention to provide a method for the treatment of mammals to correct myeloid blood production disorders by the administration of the pharmaceutical composition as aforesaid.

Other objects and advantages will become apparent to those skilled in the art from a review of the ensuing description which proceeds with reference to the following illustrative drawings.

were purified as described elsewhere (Williams, D. E., et al., EXP. HEMATOL. 15:243 (1987)).

DETAILED DESCRIPTION

In its primary aspect, the present invention concerns the identification of a class of cytokines that are believed to be implicated in the promotion of myeloid blood cell production. Specifically, these promotors of myelopoietic activity comprise a group of cytokines whose common properties are that they enhance myelopoietic colony stimulating factor activity, bind to heparin even at high salt concentrations, and induce localized inflammation characterized by polymorphonuclear cell infiltration when administered subcutaneously. The cytokines in object are identified as MIP-1 and MIP-2, and a full exposition of their origins, structures and activity profiles are set forth in commonly assigned parent applications Ser. Nos. 238,937, now abandoned and 240,078, now abandoned. The disclosures of both applications are incorporated herein by reference.

MIP-1 and MIP-2 comprise proteins of inferred sequence. Specifically, MIP-1 is known to comprise two purified peptide components that display the amino acid sequences set forth below as determined in mice.

| MIP-1α | | | | | | | | | | | | | |
|---|---|---|---|---|---|---|---|---|---|---|---|---|---|
| ALA | PRO | TYR | GLY | ALA | ASP | THR | PRO | THR | ALA | CYS | CYS | PHE | SER |
| TYR | SER | ARG | LYS | ILE | PRO | ARG | GLN | PHE | ILE | VAL | ASP | TYR | PHE |
| GLU | THR | SER | SER | LEU | CYS | SER | GLN | PRO | GLY | VAL | ILE | PHE | LEU |
| THR | LYS | ARG | ASN | ARG | GLN | ILE | CYS | ALA | ASP | SER | LYS | GLU | THR |
| TRP | VAL | GLN | GLU | TYR | ILE | THR | ASP | LEU | GLU | LEU | ASN | ALA | |

| MIP-1β | | | | | | | | | | | | | |
|---|---|---|---|---|---|---|---|---|---|---|---|---|---|
| ALA | PRO | MET | GLY | SER | ASP | PRO | PRO | THR | SER | CYS | CYS | PHE | SER |
| TYR | THR | SER | ARG | GLN | LEU | HIS | ARG | SER | PHE | VAL | MET | ASP | TYR |
| TYR | GLU | THR | SER | SER | LEU | CYS | SER | LYS | PRO | ALA | VAL | VAL | PHE |
| LEU | THR | LYS | ARG | GLY | ARG | GLN | ILE | CYS | ALA | ASN | PRO | SER | GLU |
| PRO | TRP | VAL | THR | GLU | TYR | MET | SER | ASP | LEU | GLU | LEU | ASN | |

Figure 1:
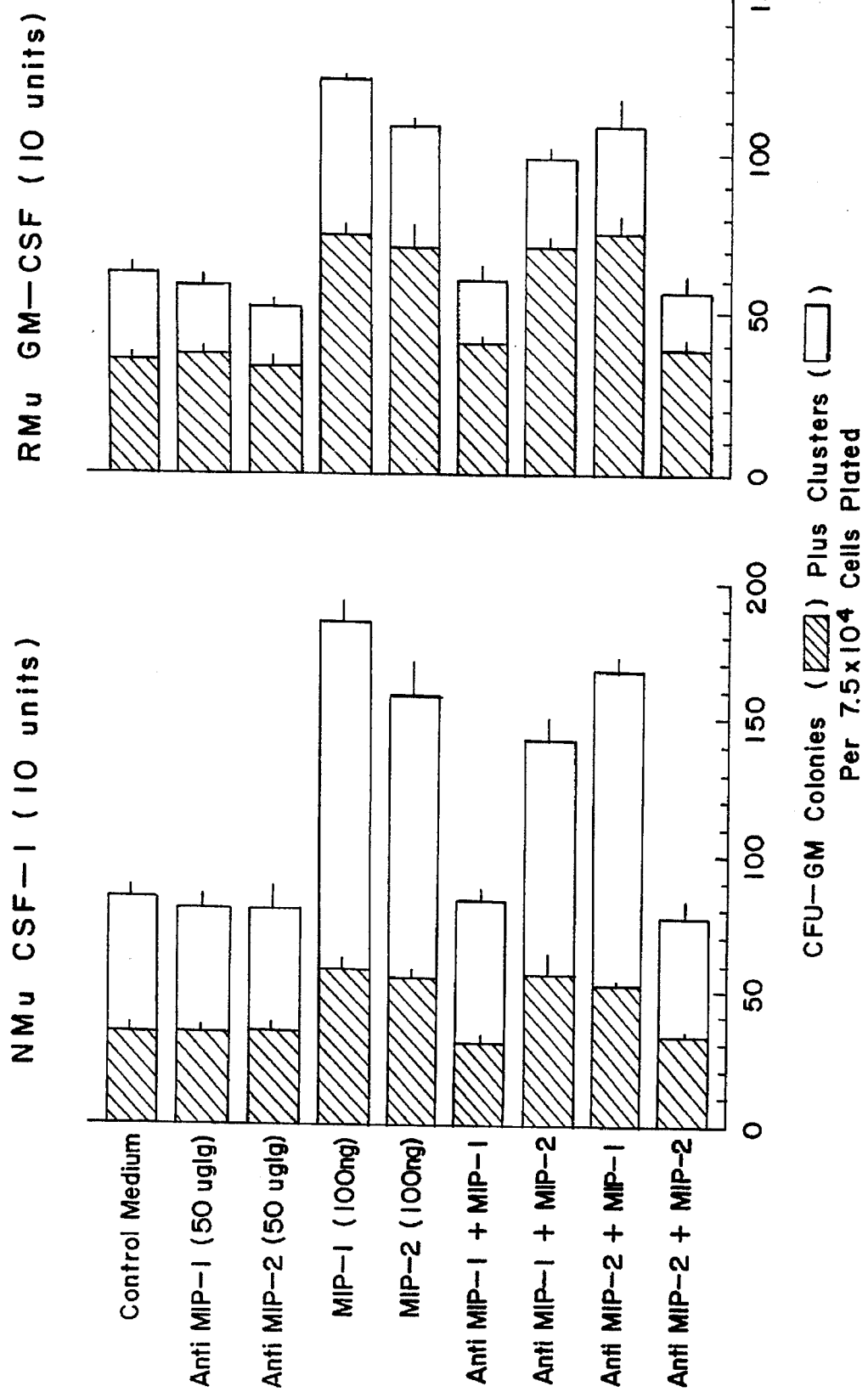
FIG. 1 shows the influence of anti-MIP-1 and anti-MIP-2 antibodies on the myeloid enhancing activity of MIP-1 and MIP-2. Preparations of MIP were preincubated with control medium or anti-MIP for 1½ hours at room temperature prior to addition to culture dishes with $5 \times 10^4$ BDF$_1$ bone marrow cells/ml in the presence of rmuCSF-1 or rmuGM-CSF. Significant increases in colony and cluster formation ($p<0.001$) were noted with MIP-1, MIP-2, anti-MIP-1 plus MIP-2, and anti-MIP-2 plus MIP-1. The other values were not significantly different from control ($p>0.05$).

| ALA | VAL | VAL | ALA | SER | GLU | LEU | ARG | CYS | GLN | CYS | LEU | LYS | THR |
|---|---|---|---|---|---|---|---|---|---|---|---|---|---|
| LEU | PRO | ARG | VAL | ASP | PHE | LYS | ASN | ILE | GLN | SER | LEU | SER | VAL |
| THR | PRO | PRO | GLY | | | | | | | | | | |

Naturally, other cell lines or other sources for the development of either the material from which the cytokines are thereafter isolated, or the inflammatory cytokines themselves, are contemplated herein and the present invention is accordingly not limited. Thus, alternate means such as by recombinant techniques are contemplated herein in accordance with the present invention and as set forth in both of the parent applications referenced earlier herein.

The heparin-binding proteins MIP-1 and MIP-2 have previously been shown to elicit a localized inflammatory response when injected s.c. into footpads of C3H/Hej mice. MIP-1 acts as a prostaglandin-independent endogenous pyrogen when administered to mice and is capable of inducing in vitro chemokinesis of human neutrophils and of triggering adherent neutrophils to release hydrogen peroxide. MIP-2 is capable of acting as a chemotactic, but not as a chemokinetic, agent for neutrophils and could induce neutrophils degranulation of lysozyme, but not of beta-glucuronidase.

The present invention is based on the discovery that agents possessing the general activity profile of the inflammatory cytokines MIP-1 and MIP-2 take part in the activity of the granulocyte-macrophage progenitor cell. While MIP-1 and MIP-2 appear to lack independent hematopoietic CSF activity, they enhance in a greater than additive fashion colony and cluster formation of bone marrow CFU-GM from mice stimulated with nmuCSF-1 and rmuGM-CSF and of bone marrow CFU-GM from normal human donors stimulated with rhuGM-CSF. Studies using purified mouse marrow CFU-GM presented later on herein suggest that the myelopoietic enhancing effects of MIP-1 and MIP-2 are due to a direct effect on the CFU-GM itself. The exact manner and mechanism of action of MIP-1 and MIP-2 on CFU-GM remains to be determined, but the action appears to be mediated, or at least initiated, during the S-phase of the cell cycle. The fact that MIP-1 and MIP-2 can act directly on CFU-GM does not however, rule out the possibility that MIP-1 and MIP-2 might be able to modulate myelopoiesis indirectly through an action on accessory cells.

As discussed earlier, the present invention includes the agents set forth above, compositions containing such agents and therapeutic methods employing such agents and compositions. Accordingly, the agents of the present invention, or their binding partner(s) or other ligands may be prepared in pharmaceutical compositions, with a suitable carrier and at a strength effective for administration by various means to a patient having a myeloid blood cell production disorder or dysfunction, for the treatment thereof. A variety of administrative techniques may be utilized, among them ex vivo bone marrow treatment, or parenteral techniques such as intravenous injection, catheterizations and the like. In particular, concentrations of the agent may range from at least about 100 ng/ml, and preferably from about 100 ng/ml to about 200 ng/ml may be used. The exact quantities of the agent administered may vary and should be based upon the recommendations and prescription of a qualified physician or veterinarian.

Antibodies and drugs may also be raised to the agent and may be utilized where appropriate for the purpose of modulating the production of myeloid blood cells by a mammalian host. In particular, the agent may be used to produce antibodies to itself in a variety of mammals, by known techniques such as the hybridoma technique utilizing, for example, fused mouse spleen lymphocytes and myeloma cells. The resulting antibodies could then be prepared in a suitable pharmaceutical composition and administered to the intended host. The exact quantities, intervals of administration and administrative techniques respecting such pharmaceutical compositions may vary in accordance with those known in the medical arts, and upon the specific instruction of a qualified physician or veterinarian.

The present invention also relates to a variety of diagnostic applications, including methods for detecting or investigating disorders or dysfunctions in myeloid blood cell production by reference to the ability of the agent of the present invention or its binding partners to promote or inhibit myelopoietic colony stimulating factor activity. As mentioned earlier, the agent or its binding partner could be appropriately labeled and placed in contact with a sample of bone marrow from a mammal in which the disorder is suspected. Thereafter, the sample could be examined to determine the location and status of the labeled material as well as the general activity of the sample, i.e. whether blood cell production has increased or decreased.

As indicated earlier, the following examples set forth the details of the investigation and identification of the CSF promoting activity of the stated inflammatory cytokines. Naturally, the specific materials and techniques set forth hereinafter are exemplary only and may vary, so that the following is presented as illustrative but not restrictive of the present invention.

EXAMPLE I

Myelopoietic Enhancing Activities in Vitro of MIP-1 and MIP-2

In this series of experiments, it was sought to be determined whether the cytokines MIP-1 and MIP-2 were involved in any way in colony and cluster formation. Accordingly, MIP-1 and MIP-2 were assessed alone and in combination, at various concentrations, for their influence on colony and cluster formation by mouse bone marrow CFU-GM stimulated with suboptimal concentrations of nmuCSF-1 or rmuGM-CSF.

Materials and Methods

Cells and Cell Separation Procedures

Femoral bone marrow cells were obtained from 4- to 6-week-old (C57B1/6×DBA/2) $F_1$ ($BDF_1$) female mice purchased from Cumberland View Farms (Clinton, Tenn.). Cells were used either unseparated or after purification as described elsewhere with minor modification (Williams, D. E., et al., EXP. HEMATOL. 15:243 (1987)). In short, purified CFU-GM were obtained as follows: mice were injected i.p. with 200 mg/kg cyclophosphamide, marrow cells were removed three days later and the low density cells (<1.077 gm/cm$^3$) were retrieved after density cut separation on Ficoll-Hypaque (Pharmacia Fine Chemicals, Piscataway, N.J.). The low density cells were then subjected to further separation by centrifugal elutriation, at 4° C. rather than 10° C., using a SANDERON (trademark) Chamber. In the present studies, the peak CFU-GM-containing fractions elutriated at a slower sedimentation rate (16–20 ml/min) than previously reported (24–28 ml/min), but the yields and purity of CFU-GM were similar.

Bone marrow cells were obtained by aspiration from the posterior iliac crest of healthy volunteers who had given informed consent according to the guidelines established by the Human Investigation Committee of the Indiana University School of Medicine. Low density marrow cells were purified on Ficoll-Hypaque and cultured.

Biomolecules and Antibodies

Natural murine MIP-1 and MIP-2 from Raw 264.7 cell supernatants were purified as described previously (Wolpe, S. D., et al., J. EXP. MED., 167:570 (1988); Davatelis, G., et al., J. EXP. MED., 167:1939 (1988); Sherry, B., et al., J. EXP. MED., 168:2251 (1988); Wolpe, S. D., et al., PROC. NATL. ACAD. SCI. USA, 86:612 (1989)). MIP-1 is recognized as a doublet of ~8000 daltons and MIP-2 as a single band of ~6000 daltons on SDS-polyacrylamide gel electrophoresis. Recombinant preparations of mu and hu GM-CSF and muIL-4 (specific activities of ~$10^8$ Units/mg each) (Broxmeyer, H. E., et al., J. IMMUNOL. 141:3852 (1988)) and huIL-6 (specific activity $5 \times 10^6$ Units/mg) were kind gifts from Dr. David Urdal and Dr. Steven Gillis, Immunex Corp., Seattle, Wash. Natural muCSF-1 (specific activity $2.3 \times 10^7$ Units/mg) (Id.) was a kind gift from Dr. Richard K. Sadduck, University of Pittsburgh School of Medicine, Pittsburgh, Pa. Recombinant huG-CSF (95% pure, specific activity $>5 \times 10^7$ Units/mg) (Id.) was a kind gift from Dr. Peter Ralph and Dr. Robert Drummond, Cetus Corporation, Emeryville, Calif. Recombinant huIL-1 alpha (specific activity $10^8$ Units/mg using the D10 cell assay) (Williams, D. E., et al., BLOOD 72:1608 (1988)) was a kind gift from Dr. Peter L. Lomedico, Hoffman-La Roche, Nutley, N.J. The purified immunoglobulin fractions against MIP-1 and MIP-2 were prepared from sera of rabbits injected respectively with SDS-PAGE gel-purified preparations of MIP-1 and MIP-2. E. coli lipopolysaccharide (LPS) was purchased from Sigma Chemical Co., St. Louis, Mo.

Colony Assays

CFU-GM:

Unseparated mouse bone marrow cells (0.5, 0.75 and $1.0 \times 10^5$ cells/ml) and low density human bone marrow cells ($1.0 \times 10^5$ cells/ml) were plated in standard 35-mm tissue culture dishes in 1 ml of 0.3% agar (Difco Laboratories, Inc., Detroit, Mich.) culture medium containing McCoy's 5A medium supplemented with additional essential and non-essential amino acids, glutamine, serine, asparagine, sodium pyruvate (GIBCO Laboratories, Grand Island, N.Y.) and inactivated (56° C. for ½ hr) 10% fetal bovine serum (Hyclone Inc., Logan, Utah) with or without purified growth factors (Broxmeyer, H. E., et al., J. IMMUNOL. 141:3852 (1988)). Purified murine CFU-GM were plated at 200 cells/ml in 0.4% agarose (Williams, D. E., et al., EXP. HEMATOL. 15:243 (1987)). Serum-free culture conditions were as described elsewhere (Lu, L., et al., CANCER RES. 46:4357 (1986)). Culture dishes were incubated at 37° C. in a humidified atmosphere flushed with 5% $CO_2$ at lowered (5%) $O_2$ tension and scored after 7 days for colonies (>50 cells/aggregate) and clusters (5 to 50 cells/aggregate) for human and mouse cells, and also after 14 days for human cells. Day 7 and day 14 colonies appear to derive from different human CFU-GM progenitors (Jacobsen, N., et al., CELL TISSUE KINET. 12:213 (1979); Ferrero, D., et al., PROC. NATL. ACAD. SCI. USA 80:4114 (1983)) and colonies-plus-clusters is a more accurate estimate of the actual number of progenitor cells stimulated than colonies only (Jacobsen, N., et al., CELL TISSUE KINET. 12:213 (1979)). Colony and cluster morphology was assessed in whole plates stained with α-naphyl acetate esterase and luxol fast blue and then counter-stained with hematoxylin (Lu, L., et al., J. IMMUNOL. 139:1823 (1987)). CFU-GM in DNA synthesis (S-phase of the cell-cycle) were killed by pulse exposure to high specific activity tritiated thymidine using 50 µCi/ml (specific activity 20 Ci/mmol, New England Nuclear, Boston, Mass.) as described (Broxmeyer, H. E., et al., J. CLIN. INVEST. 79:721 (1987); Broxmeyer, H. E., et al., EXP. HEMATOL. 16:594 (1988)).

BFU-E:

Mouse bone marrow cells ($2 \times 10^5$ cells/ml) were plated in standard 35-mm tissue culture dishes containing a 1 ml mixture of Iscove's modified Dulbecco's medium, 1.3% methylcellulose, 30% fetal bovine serum, $5 \times 10^{-5}$ M 2-mercaptoethanol, 0.1 mM hemin (Eastman Kodak Co., Rochester, N.Y.) and 2 Units tissue grade culture (r)erythropoietin (Amgen Corp., Thousand Oaks, Calif.) (Broxmeyer, H. E., et al., J. CLIN. INVEST. 79:721 (1987)). Cultures were incubated as above for CFU-GM and scored after 7 days of incubation.

Statistics

The results are expressed as the mean ±1 SEM of 3 plates per point for the CFU-GM assay and 4 plates per point for the BFU-E assay. Levels of significance for comparisons between samples were determined using student's t distribution.

RESULTS

The results of the above discussed experiments are presented in Tables 1 and 2, below.

TABLE 1

Influence of Various Concentrations of MIP-1 and MIP-2, Alone or in Combination, on Colony and Cluster Formation by Mouse Bone Marrow CFU-GM Co-stimulated in vitro with CSF-1 or GM-CSF

| | CFU-GM per $7.5 \times 10^4$ BDF$_1$ Marrow Cells Stimulated with: | | | |
| --- | --- | --- | --- | --- |
| | rmu CSF-1 (10 Units/ml) | | rmu GM-CSF (10 Units/ml) | |
| Additions to Culture: | Colonies | Colonies and Clusters | Colonies | Colonies and Clusters |
| Control Medium | 17 ± 2 | 64 ± 6 | 49 ± 2 | 61 ± 3 |
| MIP-1 (200 ng/ml) | 40 ± 4[a] | 104 ± 7[a] | 79 ± 5[a] | 101 ± 6[a] |
| MIP-1 (100 ng/ml) | 35 ± 2[a] | 100 ± 2[a] | 79 ± 1[a] | 102 ± 4[a] |
| MIP-1 (50 ng/ml) | 22 ± 2 | 57 ± 6 | 64 ± 3[a] | 84 ± 1[a] |
| MIP-1 (25 ng/ml) | 16 ± 1 | 51 ± 1 | 59 ± 2[a] | 76 ± 2[a] |
| MIP-1 (12.5 ng/ml) | 17 ± 1 | 64 ± 6 | 47 ± 3 | 61 ± 3 |
| MIP-1 (6.25 ng/ml) | 17 ± 1 | 61 ± 4 | 48 ± 2 | 60 ± 3 |
| MIP-2 (200 ng/ml) | 30 ± 2[a] | 109 ± 6[a] | 72 ± 2[a] | 89 ± 2[a] |
| MIP-2 (100 ng/ml) | 30 ± 5[a] | 103 ± 5[a] | 75 ± 6[a] | 97 ± 3[a] |
| MIP-2 (50 ng/ml) | 18 ± 2 | 68 ± 7 | 57 ± 6[a] | 71 ± 6 |
| MIP-2 (25 ng/ml) | 16 ± 1 | 59 ± 3 | 47 ± 2 | 60 ± 3 |
| MIP-2 (12.5 ng/ml) | 18 ± 3 | 60 ± 2 | 45 ± 3 | 57 ± 4 |
| MIP-2 (6.25 ng/ml) | 17 ± 2 | 61 ± 1 | 46 ± 3 | 59 ± 4 |
| MIP-1 (6.25 ng/ml) + MIP-2 (6.25 ng/ml) | 15 ± 1 | 58 ± 1 | 47 ± 2 | 61 ± 3 |
| MIP-1 (100 ng/ml) + MIP-2 (100 ng/ml) | 32 ± 2[a] | 92 ± 9[a] | 81 ± 5[a] | 94 ± 6[a] |

[a] $p < 0.05$ compared to control medium

TABLE 2

Influence of MIP-1 and MIP-2 on Colony and Cluster Formation by Mouse Bone Marrow CFU-GM Stimulated in vitro with CSF-1, GM-CSF, or G-CSF

| | Percent Increased by MIP over Numbers of CFU-GM Stimulated with CSF's alone[a] | | | |
|---|---|---|---|---|
| | Colonies | | Colonies and Clusters | |
| CSF | +MIP-1 | +MIP-2 | +MIP-1 | +MIP-2 |
| None | 0 (4) | 0 (4) | 3 ± 4 (4) | 6 ± 6 (4)[a] |
| nmuCSF-1 (10 Units/ml) | 108 ± 20 (14)[b] | 146 ± 46 (9)[b] | 59 ± 9 (14)[b] | 63 ± 7 (9)[b] |
| nmuCSF-1 (100 Units/ml) | 33 ± 5 (10)[c] | 44 ± 7 (5)[c] | 39 ± 3 (10)[c] | 43 ± 13 (5)[c] |
| rmuGM-CSF (10 Units/ml) | 55 ± 7 (12)[b] | 68 ± 8 (8)[b] | 57 ± 6 (12)[b] | 58 ± 4 (8)[b] |
| rmuGM-CSF (100 Units/ml) | 36 ± 6 (7)[c] | 40 ± 4 (5)[c] | 46 ± 8 (7)[c] | 41 ± 7 (5)[c] |
| rhuG-CSF (100 Units/ml) | 7 ± 7 (3) | 4 ± 4 (3) | 11 ± 6 (3) | 9 ± 4 (3) |

[a]Results are expressed as the mean ± 1 S.E.M., with numbers of experiments done shown in parentheses, for $BDF_1$ mouse bone marrow cells plated at $5.0 \times 10^4$, $7.5 \times 10^4$, or $1.0 \times 10^5$ cells/ml in the absence and presence of added CSF and in the absence or presence of 100 to 300 ng/ml MIP-1 or MIP-2. Results were similar regardless of the cell concentration plated or if cells were plated in the absence of presence of $10^{-6}$ M indomethacin and were therefore pooled. The increases are based on control CFU-GM numbers of: 0 colonies and 0 to 8 ± 1 colonies and clusters without CSF; 7 ± 1 to 39 ± 1 colonies and 30 ± 1 to 120 ± 10 colonies-plus-clusters with 10 Units/ml CSF-1; 62 ± 1 to 151 ± 5 colonies and 109 ± 6 to 313 ± 13 colonies-plus-clusters with 100 Units/ml CSF-1; 19 ± 1 to 49 ± 2 colonies and 28 ± 1 to 103 ± 5 colonies-plus-clusters with 10 Units/ml GM-CSF; 31 ± 1 to 67 ± 2 colonies and 45 ± 3 to 137 ± 4 colonies-plus-clusters with 100 Units/ml GM-CSF, 8 ± 1 to 15 ± 3 colonies and 19 ± 2 to 38 ± 5 colonies plus clusters with 100 Units/ml G-CSF.
[b]Increases for each experiment within these groups were statistically significant at p < 0.01.
[c]Increases for each experiment within these groups were statistically significant at p < 0.05.

Referring first to Table 1, both MIP-1 and MIP-2 significantly enhanced colony, and colony-plus-cluster, formation stimulated by 10 Units/ml of either nmuCSF-1 or rmuGM-CSF. Maximal levels of enhancement were noted at 100 to 200 ng/ml MIP-1 or MIP-2 and concentrations of up to 1000 ng/ml of MIP-1 or MIP-2 did not further enhance colony or cluster formation (data not shown). The combination of MIP-1 plus MIP-2 had no greater effect than that of either MIP-1 or MIP-2.

Referring next to Table 2, neither MIP-1 nor MIP-2, at concentrations of 100 to 300 ng/ml, stimulated colony or cluster formation of mouse marrow CFU-GM in the absence of an added source of CSF (when no colonies and few clusters formed). Either MIP-1 or MIP-2 enhanced colony and cluster formation of mouse marrow CFU-GM maximally stimulated by nmuCSF-1 or rmuCSF-1 (100 Units/ml of each), but the percent enhancement noted was not as great as that seen when colonies and clusters were stimulated with suboptimal concentrations of either CSF (10 Units/ml of either). The enhancing effects of MIP-1 or MIP-2 were similar whether colonies or colonies-plus-clusters were evaluated except when 10 Units/ml of nmuCSF-1 was used to stimulate the cells; in this case enhancement of colonies by MIP-1 or MIP-2 was greater than the enhancement for colonies-plus-clusters. The MIP enhancing effects were noted whether the cells were plated in the absence or presence of $10^{-6}$M indomethacin.

The enhancing activity of MIP-1 or MIP-2 was also apparent in the absence of serum in the culture system, and the enhancement was apparent for both colonies and clusters which contained only macrophages or which contained both macrophages and neutrophils whether cells were cultured in the presence or absence of serum. The results are presented in Tables 3 and 4, below.

TABLE 3

Influence of MIP-1 and mIP-2 on Colony and Cluster Formation by Mouse Bone Marrow Cells Stimulated by CSF-1 and GM-CSF in the Absence of Serum

| | CFU-GM/$7.5 \times 10^4$ $BDF_1$ Bone Marrow Cells | |
|---|---|---|
| Cells plated with: | Colonies | Colonies and Clusters |
| A) 100 Units/ml nmu CSF-1 | | |
| CSF-1 alone | 7 ± 2 | 18 ± 5 |
| +MIP-1 (200 ng/ml) | 12 ± 2 (+71)[a,b] | 34 ± 2 (+89)[b] |
| +MIP-2 (200 ng/nl) | 13 ± 2 (+86)[b] | 30 ± 2 (+67)[b] |
| B) 100 Units/ml rmu GM-CSF | | |
| GM-CSF alone | 9 ± 2 | 22 ± 1 |
| +MIP-1 (200 ng/ml) | 18 ± 1 (+100)[c] | 39 ± 1 (+77)[d] |
| +MIP-2 (200 ng/nl) | 20 ± 3 (+122)[c] | 43 ± 5 (+95)[d] |

[a]numbers in parentheses represent percent increased over respective control (CSF alone)
[b]p < 0.05
[c]p < 0.02
[d]p < 0.01

TABLE 4

Influence of MIP-1 and MIP-2 on Morphology of Colonies and Clusters formed from Mouse Bone Marrow CFU-GM[a]

| Additions to Culture | CSF Units/ml | −/+ Serum | Total | MΦ | MΦ-N | Total | MΦ | MΦ-N |
|---|---|---|---|---|---|---|---|---|
| Control Medium | 10 | + | 85 ± 3 | 48 | 37 | 67 ± 5 | 28 | 39 |
| 100 ng/ml MIP-1 | 10 | + | 186 ± 7[b] | 120(+120) | 66(+78) | 114 ± 2[b] | 56(+100) | 58(+49) |
| 100 ng/ml MIP-2 | 10 | + | 158 ± 12[b] | 88(+83) | 70(+89) | 103 ± 3[b] | 55(+96) | 48(+23) |
| Control Medium | 10 | + | | | | 47 ± 2 | 13 | 34 |
| 300 ng/ml MIP-1 | 10 | + | | | | 87 ± 2[b] | 34(+162) | 53(+55) |
| 300 ng/ml MIP-2 | 10 | + | | | | 82 ± 1[b] | 31(+138) | 51(+50) |
| Control Medium | 100 | + | | | | 137 ± 4 | 75 | 62 |
| 200 ng/ml MIP-1 | 100 | + | | | | 217 ± 8[b] | 123(+64) | 94(+52) |
| Control Medium | 100 | + | 166 ± 5 | 134 | 32 | 69 ± 4 | 34 | 35 |
| 300 ng/ml MIP-1 | 100 | + | 250 ± 6[b] | 203(+51) | 47(+47) | 101 ± 4[b] | 46(+35) | 55(+57) |
| 300 ng/ml MIP-2 | 100 | + | 310 ± 12[b] | 202(+51) | 108(+238) | 107 ± 5[b] | 47(+38) | 60(+71) |
| Control Medium | 100 | − | 18 ± 5[b] | 18 | 0 | 22 ± 1 | 14 | 8 |
| 200 ng/ml MIP-1 | 100 | − | 34 ± 2[b] | 34(+89) | 0 | 39 ± 1[b] | 20(+43) | 19(+138) |
| 200 ng/ml MIP-2 | 100 | − | 30 ± 2[b] | 30(+67) | 0 | 43 ± 5[b] | 18(+29) | 25(+213) |

[a]Individual results of 5 experiments expressed per $5 \times 10^4$ $BDF_1$ cells plated per ml in the presence of CSF and in the absence and presence of MIP and serum. MΦ = macrophages; MΦ-N = mixed macrophages and neutrophils.
[b]Significant increase compared to control medium, $p < 0.001$; other numbers are not significantly different from control, $p > 0.05$.

EXAMPLE II

Specificity of MIP-1 and MIP-2-Myelopoietic Enhancing Activities

In order to test whether the enhancing effects noted for MIP-1 and MIP-2 were independent, preparations of MIP-1 and MIP-2 were each preincubated with purified immunoglobulin fractions of rabbit anti-nmu MIP-1 or rabbit anti-nmu. MIP-2 antisera prior to adding the MIP-1 or MIP-2 to cultures containing 10 Units/ml of either nmuCSF-1 or rmuGM-CSF. The representative results of one of two similar experiments is shown in FIG. 1.

Referring to FIG. 1, the antibodies by themselves had no effect on CSF-stimulated colony or cluster formation. Anti-MIP-1 neutralized the myelopoietic enhancing activity of MIP-1 but not of MIP-2, and anti-MIP-2 neutralized the myelopoietic enhancing activity of MIP-2 but not of MIP-1; suggesting that the enhancing effects of MIP-1 and MIP-2 were independent and specific to the MIP molecules themselves.

While MIP-1 and MIP-2 enhanced CFU-GM colony and cluster formation stimulated by nmuCSF-1 and rmuGM-CSF as noted above (Tables 1–4), both MIP-1 and MIP-2 were without effect on colonies or clusters stimulated by rhuG-CSF (Table 2). Colonies and clusters stimulated by rhuG-CSF were >95% composed of only neutrophilic granulocytes.

MIP-1 and MIP-2 were also tested for their possible capacity to enhance erythroid progenitor cell proliferation by mouse bone marrow BFU-E stimulated in vitro with suboptimal (0.25 to 0.5 Units/ml; data not shown) or optimal (2 Units/ml) concentrations of Epo. No BFU-E colonies formed in the absence of Epo. Neither MIP-1 nor MIP-2, at concentrations ranging from 1 to 1000 ng/ml, influenced Epo-stimulated BFU-E colony formation. The above results are presented in detail in Table 5, below.

TABLE 5

Influence of MIP-1 and MIP-2 on Colony Formation by $BDF_1$ Mouse Bone Marrow Erythroid (BFU-E) Progenitor Cells

| | BFU-E Colonies | | | |
|---|---|---|---|---|
| | Exp. #1 | | Exp. #2 | |
| | No Epo | +Epo | No Epo | +Epo |
| Control Medium | 0 | 25 ± 1 | 0 | 25 ± 2 |
| MIP-1 (1 ng/ml) | 0 | 24 ± 1 | | |
| MIP-1 (10 ng/ml) | 0 | 25 ± 2 | | |
| MIP-1 (100 ng/ml) | 0 | 26 ± 2 | 0 | 25 ± 1 |
| MIP-1 (1000 ng/ml) | 0 | 23 ± 3 | 0 | 26 ± 2 |
| MIP-2 (1 ng/ml) | 0 | 27 ± 2 | | |
| MIP-2 (10 ng/ml) | 0 | 24 ± 2 | | |
| MIP-2 (100 ng/ml) | 0 | 26 ± 1 | 0 | 22 ± 2 |
| MIP-2 (1000 ng/ml) | 0 | 25 ± 1 | 0 | 25 ± 2 |

[a]$2 \times 10^5$ $BDF_1$ mouse bone marrow cells were plated in the presence of 0.1 mM hemin, and in the absence and presence of 2 Units/ml erythropoietin (Epo) and 1 to 1000 ng/ml MIP-1 or MIP-2. None of the numbers were statistically different from that of control medium ($p > 0.05$).

The myelopoietic enhancing effects of MIP-1 and MIP-2 on mouse bone marrow cells were not mimicked by rhuIL-1, rmuIL-4, rhuIL-6 or *E. coli* LPS (data not shown). RhuIL-1α and rhuIL-6, both of which are titered for activity on mouse cells, were each tested at 1, 5 and 10 ng/ml and were not found to significantly influence colony or cluster formation stimulated with 10 Units/ml of nmuCSF-1 or rmuGM-CSF, or 100 Units/ml rhuG-CSF. Moreover, neither 10 ng/ml of rhuIL-1α nor or rhuIL-6 significantly influenced colonies or clusters formed in the presence of 100 ng/ml MIP-1 or MIP-2 with 10 Units/ml of nmuCSF or rmuGM-CSF (data not shown). It has previously been shown that rmuIL-4 only enhances mouse bone marrow neutrophil colony and cluster formation in the presence of rhuG-CSF; it does not enhance neutrophil, neutrophil-macrophage, or macrophage colony or cluster formation stimulated with nmuCSF-1 or rmuGM-CSF (Broxmeyer, H. E., et al., J. IMMUNOL. 141:3852 (1988)). *E. coli* LPS tested at 0.01 to 100 μg/ml (in tenfold increments) in the absence or presence of $10^{-6}$M indomethacin did not enhance colony or cluster formation stimulated by 10 Units/ml nmuCSF-1 or rmuGM-CSF, but did, in dose-dependent fashion, suppress CSF-stimulated colonies and clusters with up to 93% inhibition apparent with 100 µg LPS/ml. The LPS-induced suppression was still apparent and only minimally counteracted when cells were plated with $10^{-6}$M indomethacin.

EXAMPLE III

Influence of MIP-1 and MIP-2 on Purified Populations of Mouse Marrow CFU-GM

Figure 2:
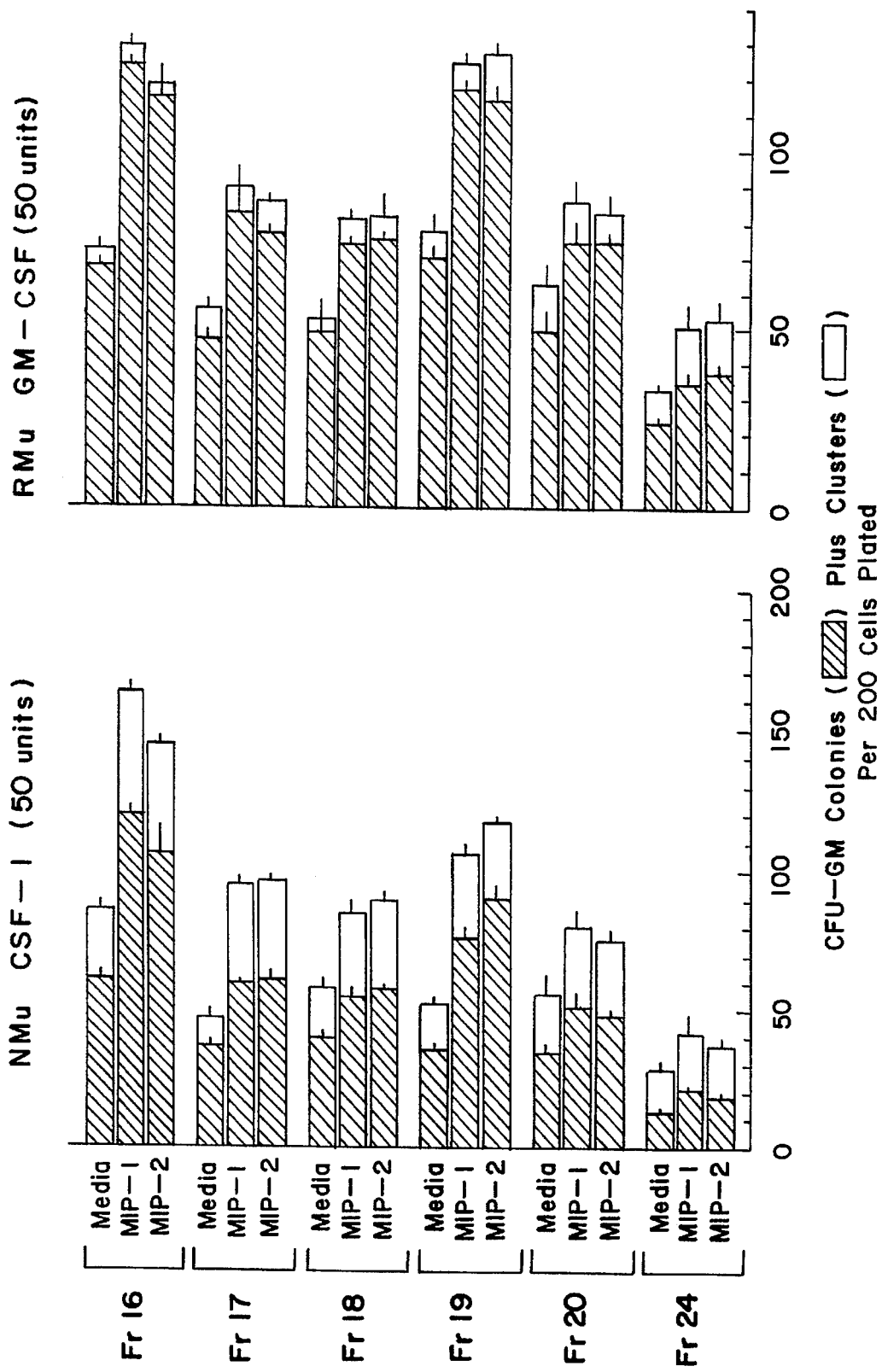
FIG. 2 depicts the influence of MIP-1 and MIP-2 on colony and cluster formation of purified mouse CFU-GM stimulated by rmuCSF-1 or rmuGM-CSF. Mouse CFU-GM Similarly, MIP-2 has been determined to possess the NH$_2$-terminal partial amino acid sequence set forth below also as determined in mice.

Since CFU-GM make up <0.5% of the population of unseparated marrow cells (as is apparent from the <0.5% colony and cluster cloning efficiency of cells plated in the presence of 100 Units/ml nmCSF-1 or rmGM-CSF in Table 2), it was not possible to determine from the above studies whether MIP-1 and MIP-2 were acting to enhance colony and cluster formation directly on the CFU-GM, or indirectly through actions on accessory cells. To determine whether MIP-1 and MIP-2 directly act on CFU-GM, mouse bone marrow cells were purified (Williams, D. E., et al., EXP. HEMATOL. 15:243 (1987)) and the preparations of MIP's were evaluated for their influence on colony and cluster formation by 200 purified cells/ml stimulated with either 50 Units/ml of nmuCSF-1 or rmuGM-CSF. The results of one representative of two similar experiments are seen in FIG. 2.

The colony plus cluster cloning efficiencies of the various fractions ranged form 15 to 44% when cells were stimulated with nmuCSF-1 and from 17 to 39% when cells were stimulated with rmuGM-CSF. These concentrations of CSF (50 Units/ml) result in maximal or near maximal stimulation of colony and cluster formation by purified CFU-GM when only one type of CSF is used, although combinations of CSFs can result in higher cloning efficiencies (Williams, D.

E., et al., EXP. HEMATOL. 15:1007 (1987)). MIP-1 and MIP-2 (100 ng/ml) each significantly enhanced (p<0.01) CSF-stimulated colony and cluster formation by purified CFU-GM in the various fractions (FIG. 2). Cloning efficiencies of up to 82% and 65% were respectively noted for cells plated in the presence of MIP plus either nmuCSF-1 or rmuGM-CSF. These results suggest that MIP-1 and MIP-2 exert direct effects on mouse marrow CFU-GM in vitro.

EXAMPLE IV

Cell-cycle Related Myelopoietic Enhancing Activities of MIP-1 and MIP-2

In order to evaluate whether MIP-1 and MIP-2 have preferential effects on CFU-GM in S-phase or during non-S-phase portions of the cell cycle, mouse bone marrow cells were pulse treated with non-radioactive (cold) thymidine or high specific activity tritiated thymidine prior to washing and plating in the presence of 10 or 100 Units/ml of nmuCSF-1 or rmuGM-CSF and in the absence or presence of 100 ng/ml MIP-1 or MIP-2. Table 6 shows the data from one of two experiments with similar results.

TABLE 6

Influence of MIP-1 and MIP-2 on Untreated Mouse Bone Marrow CFU-GM versus Bone Marrow Depleted of CFU-GM in S-Phase[a]

| Cells Plated with | Colonies | | Colonies and Clusters | |
|---|---|---|---|---|
| | Cold Tdr | $^3$HTdr | Cold Tdr | $^3$HTdr |
| A) nmu CSF-1 (10 Units/ml) | | | | |
| Control Medium | 18 ± 2 | 7 ± 1 | 60 ± 2 | 36 ± 3 |
| MIP-1 (200 Units/ml) | 32 ± 2[b] | 6 ± 1 | 105 ± 5[b] | 32 ± 2 |
| MIP-2 (200 Units/ml) | 30 ± 2[b] | 8 ± 1 | 100 ± 4[b] | 32 ± 3 |
| B) nmu CSF-1 (100 Units/ml) | | | | |
| Control Medium | 125 ± 4 | 49 ± 3 | 313 ± 13 | 180 ± 17 |
| MIP-1 (200 Units/ml) | 167 ± 9[b] | 45 ± 2 | 414 ± 7[b] | 153 ± 10 |
| MIP-2 (200 Units/ml) | 181 ± 12[b] | 52 ± 2 | 410 ± 15[b] | 196 ± 9 |
| C) rmu GM-CSF (10 Units/ml) | | | | |
| Control Medium | 41 ± 1 | 14 ± 2 | 69 ± 3 | 30 ± 3 |
| MIP-1 (200 Units/ml) | 66 ± 3[b] | 13 ± 2 | 107 ± 7[b] | 30 ± 4 |
| MIP-2 (200 Units/ml) | 72 ± 4[b] | 13 ± 1 | 104 ± 3[b] | 32 ± 2 |
| D) rmu GM-CSF (100 Units/ml) | | | | |
| Control Medium | 58 ± 4 | 26 ± 2 | 70 ± 2 | 39 ± 3 |
| MIP-1 (200 Units/ml) | 89 ± 3[b] | 25 ± 2 | 106 ± 3[b] | 40 ± 4 |
| MIP-2 (200 Units/ml) | 84 ± 3[b] | 24 ± 1 | 99 ± 1[b] | 35 ± 1 |

[a]Cells were pulse treated with cold thymidine (Tdr) or high specific activity tritiated ($^3$H) Tdr as described in the Materials and Methods section, washed and plated at $5 \times 10^4$ cells/ml in the presence of CSF and in the absence and presence of MIP-1 or MIP-2.
[b]Significant increase from control medium, p < 0.01; other numbers are not significant, p > 0.05.

Pulsing of cells with cold thymidine has been shown to have no effect on subsequent colony or cluster formation by the cells (Broxmeyer, H. E., et al., J. CLIN. INVEST. 79:721 (1987); Broxmeyer, H. E., et al., EXP. HEMATOL. 16:594 (1988)) and both MIP-1 and MIP-2 significantly enhanced colony and cluster formation by cells first pulsed with cold thymidine. In contrast, CFU-GM in DNA-synthesis (S-phase) at the time of pulse exposure with high specific activity tritiated thymidine are killed and only CFU-GM not in S-phase of the cell cycle at that time go on to proliferate in response to CSF to form a colony or cluster. MIP-1 and MIP-2 had no myelopoietic enhancing activity on cells that were first pulse treated with high specific activity tritated thymidine to remove S-phase CFU-GM. These results suggest that the myelopoietic enhancing activities of MIP-1 and MIP-2 are initiated mainly or entirely during the DNA synthetic phase of the CFU-GM cell cycle.

EXAMPLE V

Influence of MIP-1 and MIP-2 on Colony and Cluster Formation by Human Bone Marrow CFU-GM MIP-1 and MIP-2 (200 ng/ml) were evaluated for their effects on colony and cluster formation by CFU-GM present in the low density fraction of normal human bone marrow. Cells were plated at $10^5$ cells/ml in the absence or presence of 100 Units/ml rhuGM-CSF or rhuG-CSF and scored after 7 and 14 days of incubation. Low density human bone marrow cells can form colonies and clusters in the absence of an exogenously added source of CSF, but the numbers of colonies and clusters formed are related to the number of cells plated and are a result of the endogenous release of CSFs from marrow accessory cells. The results of experiments with human bone marrow are set forth in Table 7, below.

A comparison of the above data with the literature indicates that other known cytokines do not appear to mimic the myelopoietic enhancing activities of MIP-1 and MIP-2 and thus these actions appear at present to be unique ones. A number of molecules without independent CSF activity can modulate myelopoiesis in a positive fashion, but the type of enhancing activity noted for MIP-1 and MIP-2 was not duplicated by the present inventors with factors such as IL-1 alpha, IL-6, or bacterial LPS. It has previously been shown that IL-4 synergises with G-CSF to enhance neutrophil colony formation (Broxmeyer, H. E., et al., J. IMMUNOL. 141:3852 (1988)), but MIP-1 and MIP-2 did not enhance the activity of rhuG-CSF for mouse or human bone marrow cells, and IL-4 does not enhance the activities of nmuCSF-1 and rmuGM-CSF (Id.).

Also, unpublished observations indicate that IL-5 acts as an eosinophilic-CSF, and MIP-1 and MIP-2 did not stimulate or enhance eosinophil colony or cluster formation when studied by the present inventors. IL-2 has not been shown to directly enhance CFU-GM numbers (Broxmeyer, H. E., et al., CRC CRIT. REV. ONCOL./HEMATOL. 8:173 (1988)). In the type of assay used in the experiments presented herein, the tumor necrosis factors, interferons, and acidic isoferritin suppress colony formation (Broxmeyer, H. E., et al., CRC CRIT. REV. ONCOL./HEMATOL. 8:173 (1988);

TABLE 7

Influence of MIP-1 and MIP-2 on Colony and Cluster Formation by Normal Human Bone Marrow Cells[a]

| Material Added to Plate | Day 7 CFU-GM | | | | Day 14 CFU-GM | |
|---|---|---|---|---|---|---|
| | Exp. #1 | | Exp. #2 | | | |
| | Colonies | Colonies & Clusters | Colonies | Colonies & Clusters | Colonies | Colonies |
| A) No CSF | | | | | | |
| Control medium | 0 | 239 ± 22 | 0 | 149 ± 9 | 37 ± 2 | 0 |
| MIP-1 | 0 | 365 ± 16[b] | 0 | 223 ± 13[b] | 58 ± 2[b] | 0 |
| MIP-2 | 0 | 355 ± 8[b] | 0 | 170 ± 2[b] | 54 ± 6[b] | 0 |
| B) rhu GM-CSF | | | | | | |
| Control medium | 50 ± 3 | 304 ± 9 | 16 ± 2 | 162 ± 5 | 68 ± 3 | 24 ± 4 |
| MIP-1 | 88 ± 6[b] | 409 ± 11[b] | 24 ± 2b | 179 ± 9 | 125 ± 5[b] | 49 ± 6b |
| MIP-2 | 80 ± 7[b] | 398 ± 15[b] | 25 ± 3b | 173 ± 8 | 110 ± 10[b] | 45 ± 3b |
| C) rhu G-CSF | | | | | | |
| Control medium | 29 ± 2 | 183 ± 7 | 16 ± 1 | 72 ± 7 | 40 ± 3 | 16 ± 4 |
| MIP-1 | 31 ± 3 | 179 ± 7 | 17 ± 1 | 70 ± 5 | 39 ± 3 | 14 ± 3 |
| MIP-2 | 32 ± 2 | 191 ± 9 | 15 ± 1 | 66 ± 5 | 38 ± 4 | 15 ± 2 |

[a]$10^5$ low density cells/ml were plated in the absence and presence of 100 Units/ml CSF and 200 ng/ml MIP and scored for colonies and colonies-plus-clusters after 7 days of incubation and for colonies after 14 days of incubation.
[b]Significant increase compared to control medium, $p < 0.01$; other values are not significantly different from control, $p > 0.05$.

In the two experiments shown, MIP-1 and MIP-2 in the absence of added CSF significantly enhanced colony formation when colonies formed in the absence of MIP, but not when colonies did not form in the absence of MIP. MIP-1 and MIP-2 each enhanced cluster formation in the absence of exogenously added CSF. By day 7 and day 14 MIP-1 and MIP-2 had significantly enhanced colony and cluster formation by CFU-GM stimulated with rhuGM-CSF, but similar to the results noted for mouse colony and cluster formation stimulated by G-CSF (Table 2), neither MIP-1 nor MIP-2 enhanced colony or cluster formation of human bone marrow cells stimulated with rhuG-CSF.

Williams, D. E., et al., CANCER RES. 48:1548 (1988). Activin enhances and inhibin suppresses BFU-E colony formation by an action mediated through T-lymphocytes and monocytes, but has no effect on CFU-GM colony formation (Broxmeyer, H. E., et al., PROC. NATL. ACAD. SCI. USA 85:9052 (1988)). E-type prostaglandins 1 and 2 enhance BFU-E but suppress CFU-GM colony formation (Lu, L., et al., J. IMMUNOL. 139:1823 (1987)). The reported effects of transforming growth factor-beta are also not consistent with the effects noted herein for MIP-1 and MIP-2 (Sing, G. K., et al., BLOOD 72:1504 (1988); Ottman, O. G., et al., J. IMMUNOL. 140:2661 (1988)).

To summarize, the present invention is the outgrowth of in vitro experimentation with recently identified and purified murine macrophage inflammatory proteins (MIP's). MIP-1 and MIP-2 were tested alone, together, and in combination with purified recombinant (r) murine (mu) GM-CSF, natural (n)muCSF-1, or rhuman (hu)G-CSF, for effects on mouse marrow CFU-GM; in combination with erythropoietin for effects on mouse marrow BFU-E; and in combination with rhuGM-CSF or rhuG-CSF for effects on human marrow CFU-GM. MIP-1 and MIP-2 did not independently stimulate, but did enhance by up to threefold, colony formation of mouse CFU-GM co-stimulated by rmuGM-CSF and nmuCSF-1, but not by rhuG-CSF, in the absence or presence of serum.

MIP-1 and mIP-2 were maximally active at concentrations ≧100 ng/ml and the actions appeared to be initiated during the DNA synthetic portion of the cell-cycle. Neither MIP-1 nor MIP-2 at up to 1 μg/ml did not had any effect on mouse BFU-E, in the absence or presence of erythropoietin. Both MIP-1 and MIP-2 had direct-acting effects on purified mouse CFU-GM. The clonihg efficiency of 200 purified cells plated with 50 Units muCSF-1 was 82% with and 43% without MIP; the cloning efficiency with 50 Units rmuGM-CSF was 65% with and 35% without MIP.

MIP effects were not mimicked by bacterial LPS, rhuIL-1α, rhuIL-6 or rmuIL-4, and were neutralized by their own respective specific antibodies. MIP-1 and MIP-2 also enhanced endogenously-stimulated and rhuGM-CSF-stimulated, but not rhuG-CSF-stimulated colony formation by human marrow CFU-GM. These results demonstrate a new role for MIP-1 and MIP-2 in vitro as myelopoietic enhancing activities for CFU-GM.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method of stimulating granulocyte-macrophage progenitor cells in a mammalian patient in need of such treatment, comprising administering to said mammal an effective amount of a cytokine selected from the group consisting of MIP-1, MIP-2, and a mixture of MIP-1 and MIP-2, said cytokine being administered in an amount effective for granulocyte-macrophage progenitor cell colony stimulating activity.

2. The method of claim 1 wherein said cytokine is characterized by the ability to bind to heparin at high salt concentrations.

3. The method of claim 1 wherein said cytokine is administered in a concentration of at least about 100 ng/ml.

4. The method of claim 1 wherein said cytokine is administered in a concentration of from about 100 ng/ml to about 200 ng/ml.

5. The method of claim 1 wherein the cytokine has an apparent molecular weight of approximately 6000 daltons as determined by SDS-polyacrylamide gel electrophoresis.

6. The method of claim 1 wherein the cytokine has an $NH_2$-terminal partial amino acid sequence:
ALA VAL VAL ALA SER GLU LEU ARG CYS GLN CYS LEU LYS THR LEU PRO ARG VAL ASP PHE LYS ASN ILE GLN SER LEU SER VAL THR PRO PRO GLY.

7. The method of claim 1 wherein the cytokine has an apparent molecular weight of approximately 8000 daltons as determined by SDS-polyacrylamide gel electrophoresis.

8. The method of claim 1 wherein the cytokine has an amino acid sequence selected from the group consisting of

| MIP-1α | | | | | | | | | | | | | |
|---|---|---|---|---|---|---|---|---|---|---|---|---|---|
| ALA | PRO | TYR | GLY | ALA | ASP | THR | PRO | THR | ALA | CYS | CYS | PHE | SER |
| TYR | SER | ARG | LYS | ILE | PRO | ARG | GLN | PHE | ILE | VAL | ASP | TYR | PHE |
| GLU | THR | SER | SER | LEU | CYS | SER | GLN | PRO | GLY | VAL | ILE | PHE | LEU |
| THR | LYS | ARG | ASN | ARG | GLN | ILE | CYS | ALA | ASP | SER | LYS | GLU | THR |
| TRP | VAL | GLN | GLU | TYR | ILE | THR | ASP | LEU | GLU | LEU | ASN | ALA | |
| and | | | | | | | | | | | | | |
| MIP-1β | | | | | | | | | | | | | |
| ALA | PRO | MET | GLY | SER | ASP | PRO | PRO | THR | SER | CYS | CYS | PHE | SER |
| TYR | THR | SER | ARG | GLN | LEU | HIS | ARG | SER | PHE | VAL | MET | ASP | TYR |
| TYR | GLU | THR | SER | SER | LEU | CYS | SER | LYS | PRO | ALA | VAL | VAL | PHE |
| LEU | THR | LYS | ARG | GLY | ARG | GLN | ILE | CYS | ALA | ASN | PRO | SER | GLU |
| PRO | TRP | VAL | THR | GLU | TYR | MET | SER | ASP | LEU | GLU | LEU | ASN. | |

* * * * *